(12) United States Patent
Ansorge et al.

(10) Patent No.: US 7,683,034 B2
(45) Date of Patent: Mar. 23, 2010

(54) USE OF ENZYME INHIBITORS OF AMINOPEPTIDASE N AND/OR DIPEPTIDYLPEPTIDASE IV

(75) Inventors: Siegfried Ansorge, Hohenwarthe (DE); Harald Gollnick, Magdeburg (DE); Klaus Neubert, Halle (DE); Christos Zouboulis, Berlin (DE); Jurgen Faust, Halle (DE); Uwe Lendeckel, Magdeburg (DE); Dirk Reinhold, Magdeburg (DE); Robert Vetter, Magdeburg (DE)

(73) Assignee: IMTM GmbH, Magdeburg (DE)

( * ) Notice: Subject to any disclaimer, the term of this patent is extended or adjusted under 35 U.S.C. 154(b) by 749 days.

(21) Appl. No.: 10/507,548

(22) PCT Filed: Mar. 7, 2003

(86) PCT No.: PCT/EP03/02356

§ 371 (c)(1),
(2), (4) Date: Jul. 18, 2005

(87) PCT Pub. No.: WO03/077935

PCT Pub. Date: Sep. 25, 2003

(65) Prior Publication Data

US 2006/0040850 A1 Feb. 23, 2006

(30) Foreign Application Priority Data

Mar. 15, 2002 (DE) ................ 102 11 555

(51) Int. Cl.
*A61K 31/40* (2006.01)
*A61K 31/662* (2006.01)
*A61K 38/05* (2006.01)
*A61K 38/07* (2006.01)

(52) U.S. Cl. .......... 514/19; 514/18; 514/114; 514/119; 514/317; 514/330; 514/365; 514/423; 530/331

(58) Field of Classification Search ............ 514/19, 514/18, 114, 119, 317, 330, 365, 423; 530/331
See application file for complete search history.

(56) References Cited

U.S. PATENT DOCUMENTS 7,229,969 B2 * 6/2007 Ansorge et al. ............ 514/18
2005/0014699 A1 * 1/2005 Ansorge et al. ............ 514/19

FOREIGN PATENT DOCUMENTS

| DE | 101 00 053 A1 | 8/2002 |
| DE | 101 02 392 A1 | 8/2002 |
| DE | 101 55 092 A1 | 6/2003 |
| WO | WO 02053170 A2 * | 7/2002 |

OTHER PUBLICATIONS

Harper et a. Acne Vulgaris, updated Jul. 15, 2008, The Medscape Journal, emedicine web site http://www.emedicine.com/derm/TOP1C2.HTM, pp. 1-20.*

* cited by examiner

*Primary Examiner*—Cecilia Tsang
*Assistant Examiner*—Abdel A Mohamed
(74) *Attorney, Agent, or Firm*—Hodgson Russ LLP

(57) ABSTRACT

The invention relates to a process for the-inhibition of the DNA synthesis necessary for the proliferation of human sebaceous cells (sebocytes) by the isolated or joint effect of inhibitors of alanyl aminopeptidase (APN) and dipetidyl peptidase IV (DP IV) expressed by these cells. The DNA synthesis (proliferation) of human sebaceous cells is inhibited by the administration of the inhibitors of APN and/or of DP IV depending on the dose. Our invention shows that, for a therapy and for a prevention of dermatological diseases with sebaceous hyperproliferation and modified conditions of differentiation, the application of inhibitors of the above-mentioned enzymes and of corresponding pharmaceutical preparations and dosage forms thereof is suitable.

4 Claims, 3 Drawing Sheets

USE OF ENZYME INHIBITORS OF AMINOPEPTIDASE N AND/OR DIPEPTIDYLPEPTIDASE IV

This application claims priority to International Application No. PCT/EP03/02356, filed on Mar. 7, 2003, the disclosure of which is incorporated herein by reference.

The invention describes the inhibition of the DNA synthesis necessary for the proliferation of sebaceous cells (sebocytes) by the action of inhibitors of amino peptidase N(APN; E.C. 3.4.11.2.; CD13) and/or of dipeptidyl peptidase IV (DP IV; E.C. 3.4.14.5.; CD26) as the result of the separate, of the simultaneous or, with respect to the time, of the immediately successive application of respective specific inhibitors of these enzymes or of inhibitors of enzymes having a similar substrate specificity (APN- and/or DP IV-analogous enzyme activity) on the basis of amino acid derivatives, peptides or peptide derivatives by which the proliferation (DNA synthesis) of sebocytes is suppressed.

A number of dermatological diseases are associated with hyperproliferation and modified states of differentiation of sebocytes. Among them are both benign follicular hyperproliferation conditions (acne, acneiform follicular reactions, steatocystoma multiplex, naevi of sebaceous glands, senile sebaceous gland hypertrophy, seborrhea of the skin and of the hair) and malign follicular hyperproliferation conditions (mixed tumors, sebaceomes, sebaceous gland tumors, sebaceous gland CA).

Peptidases, as for example, dipeptidyl peptidase IV and amino peptidase N or similarly acting enzymes are of particular interest for a regulation and/or modulation of interactions between cells, since they are, in part, localized in the plasma membrane of the cells as ectoenzymes, interact with other extracellular structures, activate or inactivate peptiderge messenger substances by enzyme-catalyzed hydrolysis, and, hence, are important for a cell-to-cell communication. [Yaron A., et al.: Proline-dependent structural and biological properties of peptides and proteins. Crit. Rev. Biochem. Mol. Biol. 1993; 28 : 31-81; Vanhoof G., et al.: Proline motifs in peptides and their biological processing. FASEB J. 1995; 9: 736-744].

It was shown that membrane-allocated peptidases like DP IV or APN play a key role in the process of an activation and clonal expansion of immune cells, in particular of T-lymphocytes. [Fleischer B.: CD26 a surface protease involved in T-cell activation. Immunology Today 1994; 15: 180-184; Lendeckel U. et al.: Role of alanyl aminopeptidase in growth and function of human T cells. International Journal of Molecular Medicine 1999; 4: 17-27; Riemann D. et al.: CD13—not just a marker in leukemia typing. Immunology Today 1999; 20: 83-88]. Several functions of mitogene-stimulated mononuclear cells (MNZ) or of enriched T lymphocytes as, for example DNA-synthesis, production and secretion of immunostimulating cytokines (IL-2, IL-6, IL-12, IFN-γ) and helper functions for B-cells (IgG synthesis and IgM synthesis) may be inhibited in the presence of specific inhibitors of DP IV or of APN [Schön E., et al.: The dipeptidyl peptidase IV, a membrane enzyme involved in the proliferation of T lymphocytes. Biomed. Biochim. Acta 1985; 2: K9-K15; Schön E., et al.: The role of dipeptidyl peptidase IV in human T lymphocyte activation. Inhibitors and antibodies against dipeptidyl peptidase IV suppress lymphocyte proliferation and immunoglobulin synthesis in vitro. Eur. J. Immunol. 1987; 17: 1821-1826; Reinhold D., et al.: Inhibitors of dipeptidyl peptidase IV induce secretion of transforming growth factor β1 in PWM-stimulated PBMNC and T cells. Immunology 1997; 91: 354-360; Lendeckel U., et al.: Induction of the membrane alanyl aminopeptidase gene and surface expression in human T-cells by mitogenic activation. Biochem. J. 1996; 319: 817-823; Kähne T., et al.: Dipeptidyl peptidase IV: A cell surface peptidase involved in regulating T cell growth (Review). Int. J. Mol. Med. 1999; 4: 3-15; Lendeckel U., et al.: Role of alanyl amitiopeptidase in growth and function of human T cells (Review). Int. J. Mol. Med. 1999; 4: 17-27].

It is already known that a treatment of autoimmune diseases and transplant rejection may be achieved by an inhibition of dipeptidyl peptidase IV localized on immune cells by means of synthetic inhibitors (see, for example, EP-A 0 764 151; WO 095/29,691; EP-A 0 731 789; EP-A 0 528 858).

The invention is based on the surprising finding that the single or simultaneous effect of inhibitors of the dipeptidyl peptidase IV/CD26 and/or inhibitors of the amino peptidase N/CD13 or of inhibitors of enzymes having a similar substrate specifity (APN-and/or DP IV-analogous enzyme activity), expressed on or in sebaceous cells (sebocytes) inhibits the proliferation (DNS synthesis) of these cells.

Our invention shows that, for a therapy and for a prevention of dermatological diseases with sebaceous hyperproliferation and modified conditions of differentiation (benign follicular hyperproliferation conditions like acne, acneiform follicular reactions, steatocystoma multiplex, naevi of sebaceous glands, senile sebaceous gland hypertrophy, seborrhea of the skin and of the hair as well as malign follicular hyperproliferation conditions like mixed tumors, sebaceomes, sebaceous gland tumors, sebaceous gland CA) for the generation of which the proliferation of sebocytes has a central importance, the single or simultaneous application of inhibitors of DP IV and of APN or of inhibitors of enzymes having a similar substrate specificity (APN- and/or DP IV-analogous enzyme activity) or of corresponding pharmaceutical preparations and dosage forms thereof is suitable.

In detail, the invention is based on the findings that the DNA synthesis of sebaceous cells (sebocytes) is significantly inhibited by the administration of inhibitors of dipeptidyl petidase IV and/or of inhibitors of amino peptidase N.

Up to now, the above mentioned diseases are treated topically and/or systemically by administering antibiotics and/or antiproliferative and differentiating substances (antiandrogens, 13-cis-retinic acid and others). In the systemical treatment in particular, undesired side effects are often observed, inter alia teratogenicity, lipid metabolic disorders, psychoreactive phenomena, gastrointestinal disorders as well as mucocutane irritative reactions.

The use of DP IV and/or APN inhibitors would represent a completely new, presumably very effective, possibly cost effective therapy form and a valuable alternative component of existing therapy concepts of the above-referenced diseases.

The inhibitors of dipetidyl peptidase IV and/or the inhibitors of amino peptidase N or inhibitors of enzymes having a similar substrate specificity (APN-analogous and/or DP IV-analogous enzyme activity) applied according to the invention may be administered in pharmaceutically applicable formulation complexes as inhibitors, substrates, pseudo substrates, inhibitory active peptides and peptide derivatives as well as antibodies to those enzymes.

Preferred effectors for DP IV, are for example, Xaa -Pro-dipeptides, corresponding derivatives, preferably dipeptide phosphonic acid diaryl esters and their salts, dipeptide boronic acides (e.g. Pro-boro-Pro) and their salts, Xaa-Xaa-(Trp)-Pro-(Xaa)n peptides (n=0 to 10), corresponding derivatives and their salts or amino acid (Xaa)-amides, corresponding derivatives and their salts, wherein Xaa is an αamino acid/imino acid or an α-amino acid derivative/imino acid derivative, preferably N^ε-4-nitrobenzyl oxycarbonyl-L-lysine, L-proline, L-tryptophane, L-isoleucine, L-valine, and cyclic amines, e.g. pyrrolidine, piperidine, thiazolidine, and their derivatives act as amide structure, tryptophane-1,2,3,4-tetrahydroisochinoline-3-carboxylic acid derivatives (TSL) and/or (2S,2S',2S")-2-[2'-[2"-amino-3"'-(indol-3"'-yl)-1"-oxoprolyl]-1',2',3',4'-tetrahydro-6'8'-dihydroxy-7-methoxyisochinol-3-yl-carbonyl-amino]-4-hydromethyl-5-hydropentanoic acid (TMC-2A). Such compounds and their preparation were described in an earlier patent (K. Neubert et al. DD 296075A5). Preferred inhibitors for the alanyl amino peptidase are actinonin, bestatin (ubenimex), probestin, phebestin, RB3014, leuhistin, amastatin, β-aminothiols, α-aminophosphinic acids, α-amino phosphinic acid derivatives, preferably D-Pheψ-[PO(OH)—CH$_2$]-Phe-Phe.

The inhibitors or pharmaceutical compositions containing them are administered simultaneously with known carrier substances. On the one hand, the administration occurs as a topical application in the form of, for example, creams, ointments, pastes, gels, solutions, sprays, liposomes and nanosomes, lotions (agitated mixtures), hydrocolloid dressings, plasters and similar novel carrier substrates, jet injections or other dermatological bases/vehicles, including instillative applications, and on the other hand, as a systemic application for oral, transdermal, intravenous, subcutaneous, intracutaneous, intramuscular use in suitable formulations or in a suitable galenic form.

EXAMPLE 1

Inhibition of the DNA Synthesis of the Immortalized Human Sebaceous Cell Line SZ95 by the Incubation with Synthetic Inhibitors of DP IV and/or APN Our investigations show that the DNA synthesis of the immortalized human sebaceous cell line SZ95 (Zouboulis, C. C. et al.: Establishment and characterization of an immortalized human sebaceous gland cell line (SZ95), J. Invest. Dermatol. 1999, 113, 1011-1020) is inhibited by the administration of inhibitors of the DP IV (Lys[Z(NO$_2$)]-thiazolidide and/or of the APN (actinonin) in a dose-dependent manner.

The human sebaceous cell line SZ95, which is accepted as a cell model for acne, expresses strongly DP IV and APN (FIG. 1). The enzyme activity of the DP IV of vital cells amounts to 38±18 pkat/$10^6$ cells, and that of the APN amounts to 262±58 pkat/$10^6$ cells (n=3). Accordingly, the mRNA of APN and DP IV is detectable on these cells (FIG. 2).

FIG. 1 depicts cytometric flow rate verification of the expression of DP IV (CD26) and APN (CD 13) on SZ95 cells.

SZ95 cells were 48 h incubated with the above-mentioned inhibitors and subsequently the DNA synthesis was determined by the measurement of the .sup. 3[H]-Thymidine incorporation as described in Reinhold et al. (Reinhold, D. et al.: Inhibitors of dipeptidyl peptidase IV induce secretion of transforming growth factor .beta.1 in PWM-stimulated PBMNC and T-cells; Immunology, 1997, 91; 354-360). FIG. 3 shows the inhibition of the DNA synthesis depending on the dose.

Figure 1:
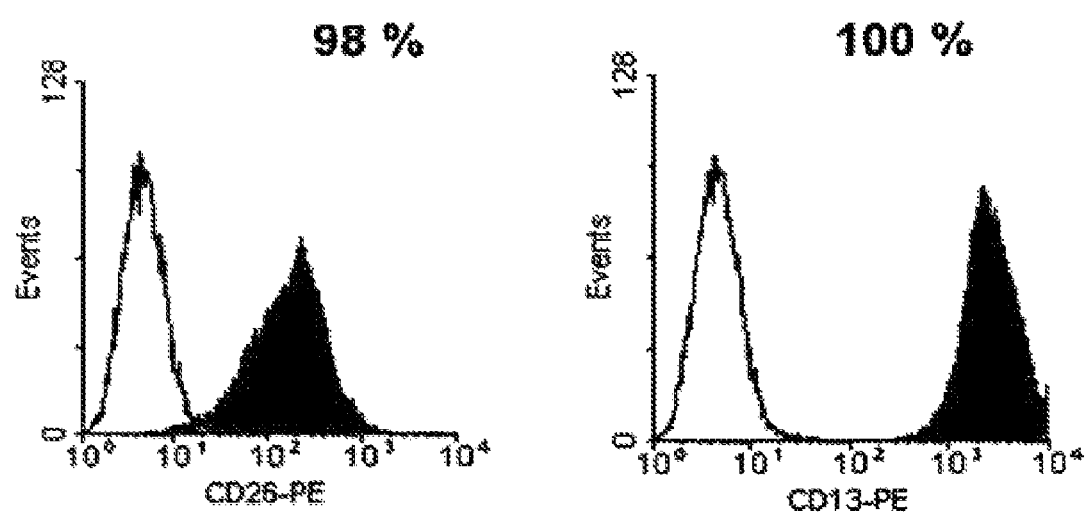
Figure 2:
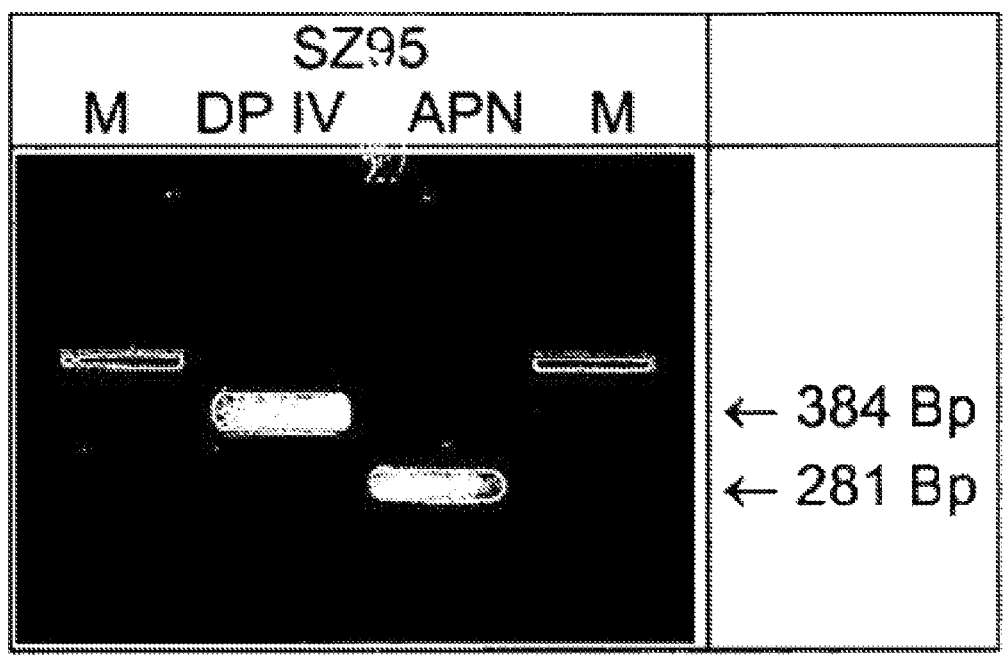
FIG. 2 depicts verification of the mRNA expression of DP IV (CD26) and APN (CD 13) on SZ95 cells via RT-PCR.
Figure 3:
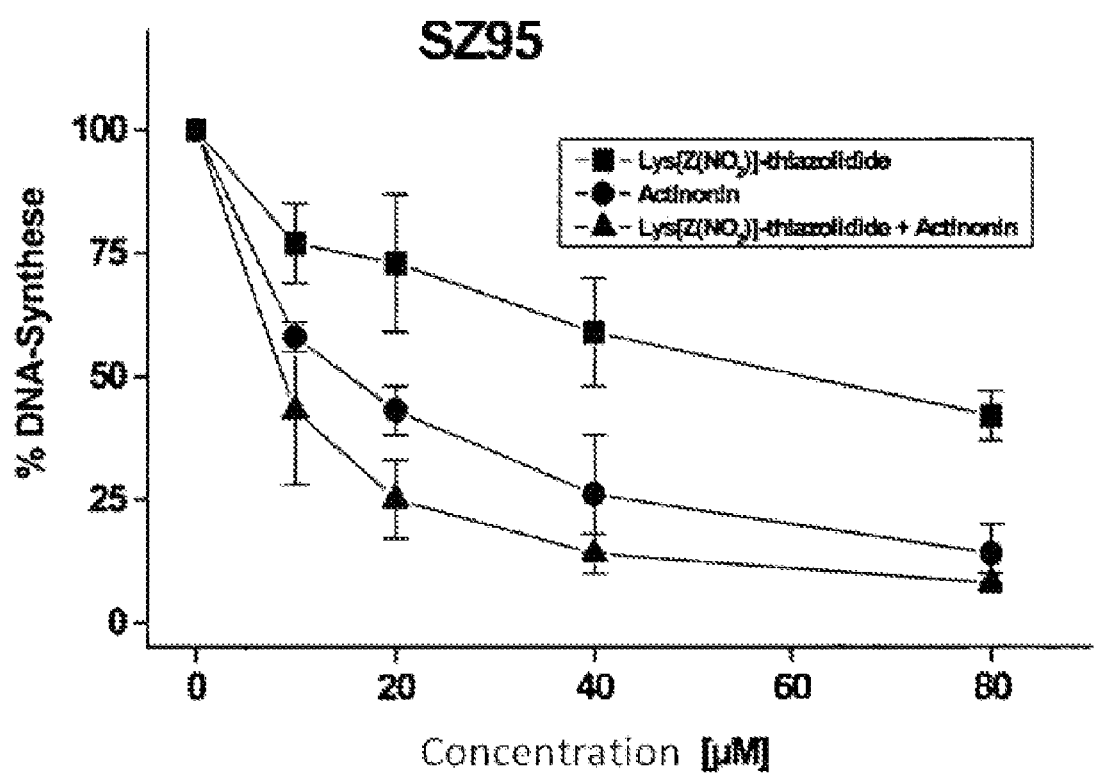
FIG. 3 depicts effect of inhibitors of the DP IV (Lys[Z(NO.sub.2)]-thiazolidide) and of the amino peptidase N (actinonin) on the DNA synthesis of human SZ95 sebaceous cells depending on the dose.

The cells were 48 h incubated with inhibitors in the above-mentioned concentrations. Subsequently $^3$[H]-Methyl-thymidin was added to the culture medium. After 6 further hours the amount of $^3$[H]-Thymidine incorporated in the DNA was measured.

The invention claimed is:

1. A method for therapy of acne and/or acneiform follicular reaction in an individual in need of the therapy comprising administering to the individual a composition comprising inhibitors of dipeptidylpeptidase IV (DP IV) as well as of inhibitors of enzymes having a similar substrate specificity (DP IV-analogous enzyme activity) and/or of inhibitors of alanyl aminopeptidase (aminopeptidase N, APN) as well as of inhibitors of enzymes having a similar substrate specificity (APN-analogous enzyme activity) for the inhibition of the proliferation (DNA synthesis) of human sebaceous cells.

2. The method according to claim 1, wherein the inhibitors of the DP IV are selected from Xaa-Pro-dipeptides (Xaa-α-amino acid or side-chain protected derivative), corresponding derivatives, preferably dipeptide phosphonic acid diaryl esters and their salts, dipeptide boronic acids (e.g. Pro-boro-Pro) and their salts, Xaa-Xaa-(Trp)-Pro-(Xaa)n peptides (Xaa=α-amino acid, n=0 to 10), corresponding derivatives and their salts, amino acid (Xaa) amides, corresponding derivatives and their salts, wherein Xaa is an α-amino acid or a side chain-protected derivative, preferably N^ε-4-nitrobenzyloxy carbonyl-L-lysine, L-isoleucine, L-valine, L-tryptophan, L-proline, and cyclic amines, for example pyrrolidine, piperidine, thiazolidine and their derivatives act as the amide structure, tryptophane- 1,2,3, 4-tetrahydroisochinoline-3-carboxylic acid derivatives (TSL) and/or (2S,2S',2S")-2-[2'-[2"-amino-3"'-(indol-3"'-yl)-1"-oxoprolyl-1',2',3',4'-tetrahydro-6'8'-dihydroxy-7-methoxyisochinol-3-yl-carbonyl-amino]-4-hydromethyl-5-hydropentanoic acid (TMC-2A).

3. The method according to claim 1, wherein amino acid amides are used as DP IV inhibitors, preferably N^ε-4nitrobenzyl oxycarbonyl-L-lysine thiazolidide, pyrrolidide and piperidide as well as the corresponding 2-cyano thiazolidide, 2-cyano pyrrolidide and 2-cyano piperidide derivative.

4. The method of claim 1 further comprising a a repeated administration of the composition.

* * * * *

UNITED STATES PATENT AND TRADEMARK OFFICE
CERTIFICATE OF CORRECTION

PATENT NO. : 7,683,034 B2  Page 1 of 1
APPLICATION NO. : 10/507548
DATED : March 23, 2010
INVENTOR(S) : Ansorge et al.

It is certified that error appears in the above-identified patent and that said Letters Patent is hereby corrected as shown below:

Claim 4, line 1 (column 4 line 51 of the issued patent), please delete "comprising a a repeated" and replace it with --comprising a repeated--.

Signed and Sealed this

Twenty-fourth Day of August, 2010

David J. Kappos
*Director of the United States Patent and Trademark Office*